United States Patent [19]

Birmingham et al.

[11] Patent Number: 4,520,819

[45] Date of Patent: Jun. 4, 1985

[54] TOURNIQUET WITH DIFFERENTIAL PRESSURE OCCLUSION DETECTOR

[75] Inventors: Michael J. Birmingham, Denver; Michael R. Manes, Littleton, both of Colo.

[73] Assignee: Aspen Laboratories, Inc., Englewood, Colo.

[21] Appl. No.: 485,346

[22] Filed: Apr. 15, 1983

[51] Int. Cl.³ .............................................. A61B 17/12
[52] U.S. Cl. .................................................... 128/327
[58] Field of Search ................ 128/327, 682, 686, 678

[56] References Cited

FOREIGN PATENT DOCUMENTS 2085198 4/1982 United Kingdom ............... 128/327

Primary Examiner—Michael H. Thaler
Attorney, Agent, or Firm—Paul David Schoenle

[57] ABSTRACT

An automatic tourniquet with an improved occlusion detector. A pump and valve for inflating and deflating a tourniquet cuff are connected to a first port. A pressure transducer for sensing the pressure in the cuff is connected to a second port. A pair of pressure differential switches, which activate an alarm when a pressure difference developes across them, are connected anti-parallelly between the pump/valve and the transducer. The differential switches also deactivate the pump/valve upon detection of an occlusion.

4 Claims, 5 Drawing Figures 4,520,819

TOURNIQUET WITH DIFFERENTIAL PRESSURE OCCLUSION DETECTOR

BACKGROUND OF THE INVENTION

1. Field of the Invention

The invention in general relates to the field of medical pneumatic tourniquets, and more particularly to a tourniquet which is automatically controlled to maintain the desired tourniquet pressure.

2. Description of the Prior Art

Tourniquets are used in medicine to stop the flow of blood into a patient's limb. A typical use is to provide a "bloodless field" in which surgical procedures may be performed on a limb, without the field being obscured by blood, and without loss of blood to the patient. Tourniquets are also used in emergency procedures to prevent loss of blood when a limb is damaged or in any other instance where it is desired to prevent blood flow to a limb.

Tourniquets conventionally consist of an inflatable cuff which is wrapped around the patient's limb, and a source of compressed gas for inflating the cuff. In order to successfully stop the flow of blood the pressure in the cuff must be above the highest level of the patient's blood pressure. However, it should not be so high that it damages the tissue of the limb. Thus in conventional tourniquets a pressure gauge for measuring the cuff pressure, and a pressure regulating mechanism is provided.

Up until very recently, conventional pneumatic tourniquets have been manually controlled mechanical devices. That it, a mechanical pressure regulating mechanism indicated the pressure and the pressure was adjusted by an attendant using a mechanical valve.

Recently, an automatic tourniquet for medical use has been created by Dr. James A. McEwen. This tourniquet is described in U.S. patent application Ser. No. 193,145 filed Oct. 2, 1980. An improved automatic tourniquet is described in U.S. patent application Ser. No. 337,152 filed Jan. 5, 1982, also by Dr. James McEwen. In these automatic tourniquets, the pressure in the cuff is continuously sensed and adjusted by a microprocessor. In addition, the microprocessor activates alarms if a dangerous pressure condition is sensed. It has been found that such automatic tourniquets systems not only are much more convenient in the operating room setting, but also significantly reduce the incidence of limb paralysis, nerve damage and other injuries attributable to tourniquets.

The above-described tourniquets are designed for use with a dual port cuff. The inflation and deflation mechanism is connected to one port of the cuff, and the pressure sensing means is connected to the other port of the cuff. This design is preferable to a single port design since it insures that the pressure sensor is responding to the pressure in the cuff, and not merely the pressure of the pressurizing means. The prior art devices also include a means intended to detect occlusions between the pressurizing means in the cuff and the pressure sensor in the cuff. The most common such occlusion is a kink in either the line between the pressurizing means and the cuff or the line between the pressure sensing means and the cuff. Thus the occlusion detector has generally become known as a kink detector.

The prior art kink detectors consist of a system which sounds an alarm if the pressurizing means attempts to inflate or deflate the cuff and the pressure sensing means does not respond as it is expected it should.

The prior art kink detectors respond to a number of other system defects in addition to occlusions. For example, they may respond to problems in the pumping system, the sensing system, or leaks in the system. Such non-specific alarms may result in delays in detecting the precise cause of the alarm. Such delays are undesirable in the surgical environment. Further, the prior art occlusion detection systems must be sophisticated, since they must be able to accurately anticipate what the response of the pressure sensor should be to activities of the pressurizing system. This response is not always simple because the pressurizing system and the sensing system are separated by a considerable length of narrow tubing and the cuff, which results in a delay between the activity of pressurizing system and the response of the sensing system.

SUMMARY OF THE INVENTION

It is an object of the invention to provide an automatic tourniquet that detects occlusions in the tourniquet fluid system simply and reliably.

It is another object of the invention to provide an automatic tourniquet with an occlusion detector that responds only to occlusions.

The invention provides a pneumatic tourniquet comprising a first means for inflating and deflating a tourniquet cuff having a first port for connection to the cuff, a second means for sensing the pressure in the cuff having a second port for connection to the cuff, a pressure differential means connected between the first and second means for producing a signal indicative of a pressure differential between the first and second means, and a means responsive to the signal for producing an alarm. Preferably the pressure differential means comprises a pair of pressure differential switches which are connected anti-parallelly between the first and second means. Preferably the pressure differential means produces the signal if the magnitude of the pressure difference between the first and second means exceeds a predetermined amount. Preferably, the alarm is an audio or visual alarm.

Numerous other aspects, features, objects, and advantages of the invention will now become apparent from the following detailed description when read in conjunction with the accompanying drawings, in which:

DESCRIPTION OF THE PREFERRED EMBODIMENT

Figure 1:
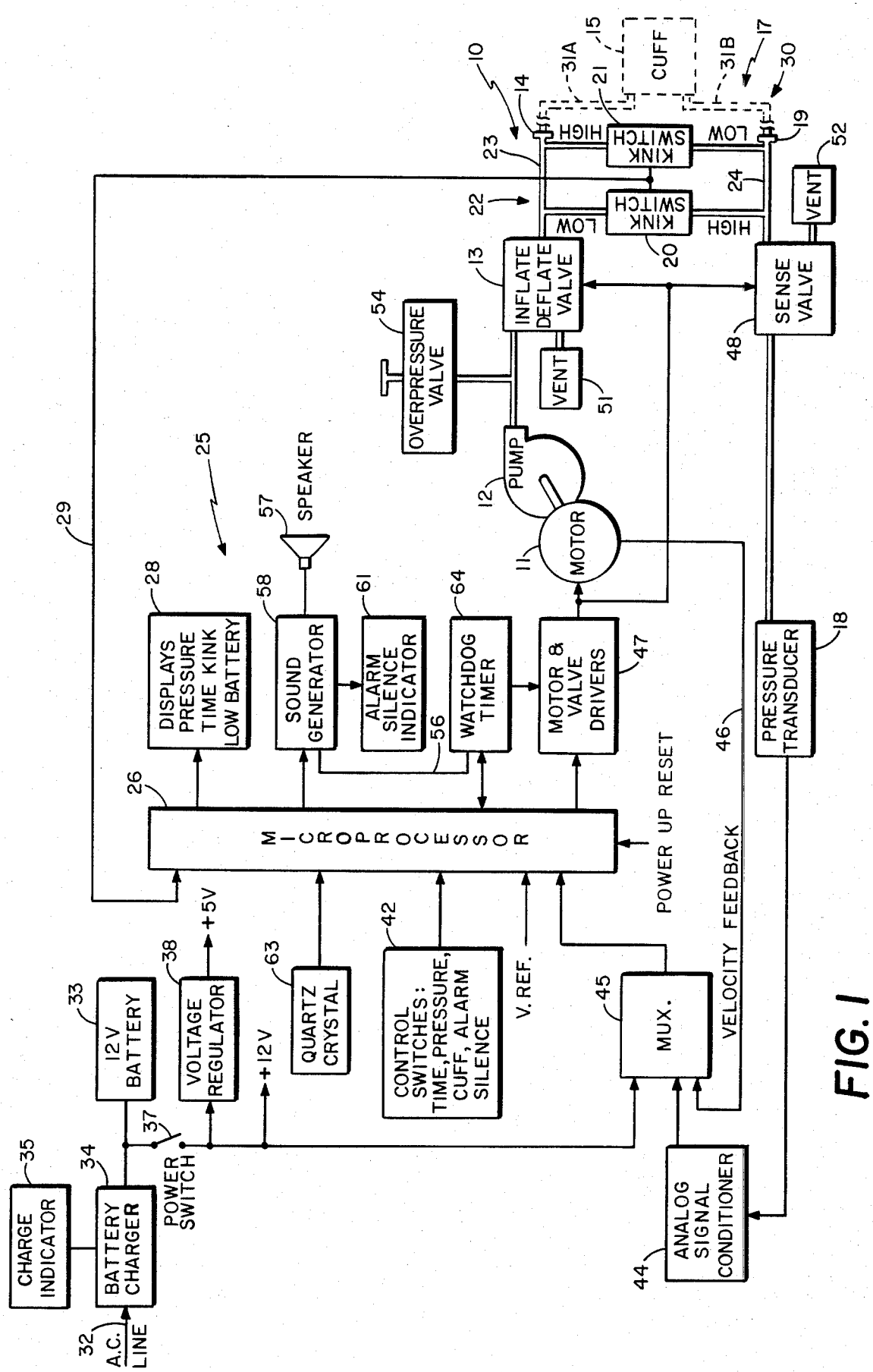
FIG. 1 is a block diagrammatic illustration of the preferred embodiment of a pneumatic tourniquet according to the invention.

Referring to FIG. 1, a pneumatic tourniquet according to the preferred embodiment of the invention is shown. A means 10 for inflating and deflating a tourniquet cuff 15, includes a motor 11, pump 12 and inflate/deflate valve 13 which are connected to cuff 15 via port 14. A means 17 for sensing the pressure of the cuff 15 includes pressure transducer 18 which is connected to cuff 15 via port 19. A pressure differential means 22, including kink switches 20 and 21, is connected between inflation/deflation line 23 and pressure sensing line 24, and produces a signal indicitative of a pressure differential between the inflation and deflation means 10 and the pressure sensing means 17. A means 25 for producing an alarm consists of microprocessor 26 and displays 28, and is responsive to the signal produced by the pressure differential means 22 via electrical line 29.

Turning now to a more detailed description of the automatic tourniquet according to the invention, power for the tourniquet is applied via AC line 32 or by battery 33. During AC operation battery charger maintains battery 33 in a charged condition. The charge indicator 35 indicates when the battery is being charged. Power is applied to the tourniquet via power switch 37. A 5-volt power supply is provided to appropriate circuits via voltage regulator 38 and a 12-volt power supply is provided to other circuits. Control switches 42 provide a means for inputing information into the microprocessor 26, including the desired tourniquet pressure. The pressure sensed by pressure transducer 18 is input into microprocessor 26 via analog signal conditioner 44 and multiplexer 45. Information regarding the motor speed is also input into microprocessor 26 via line 46 and multiplexer 45. Using the input information microprocessor 26 determines adjustments to be made in the pressure and applies a signal to motor and valve drivers 47 which in turn applies signals to motor 11, and valves 13 and 49 to control the pressure in cuff 15. For quietness, when it is desired to deflate cuff 15 gas is vented through muffled vents 51 or 52. Overpressure valve 54 provides a manually controlled safety valve, in case all other safety features of the system fail.

Microprocessor 26 is responsive to the signal from differential pressure means 22 on line 29 to apply a signal to displays 28 to produce a visual alarm, and to speaker 57 via sound generator 58 to produce an audio alarm, when an obstruction in the fluid lines 30 associated with cuff 15 is detected. These alarms may be temporarily silenced via switches 42, in which case a signal is applied via microprocessor 26 and sound generator 58 to alarm silence indicator 61. The timing for the microprocessor is provided by a signal from quartz crystal 63. Watchdog timer 64 communicates with microprocessor 26 to detect any timing errors in the microprocessor. If a timing error is detected, watchdog timer 64 provides a signal to motor and valve drivers 47 to isolate cuff 15 from the inflation and deflation means 10, and via line 56 causes an audible alarm to be sounded. If an obstruction is sensed by kink switches 20 or 21, the signal that is normally applied to motor and valve drivers 47 is not generated by the microprocessor 26, which also effectively deactivates the inflating and deflating means 10. Signals are also applied by the microprocessor 26 to the displays 28 to indicate the selected and the sensed pressure, the time the tourniquet has been on, the selected alarm time setting, and the condition of the battery 34.

Figure 2:
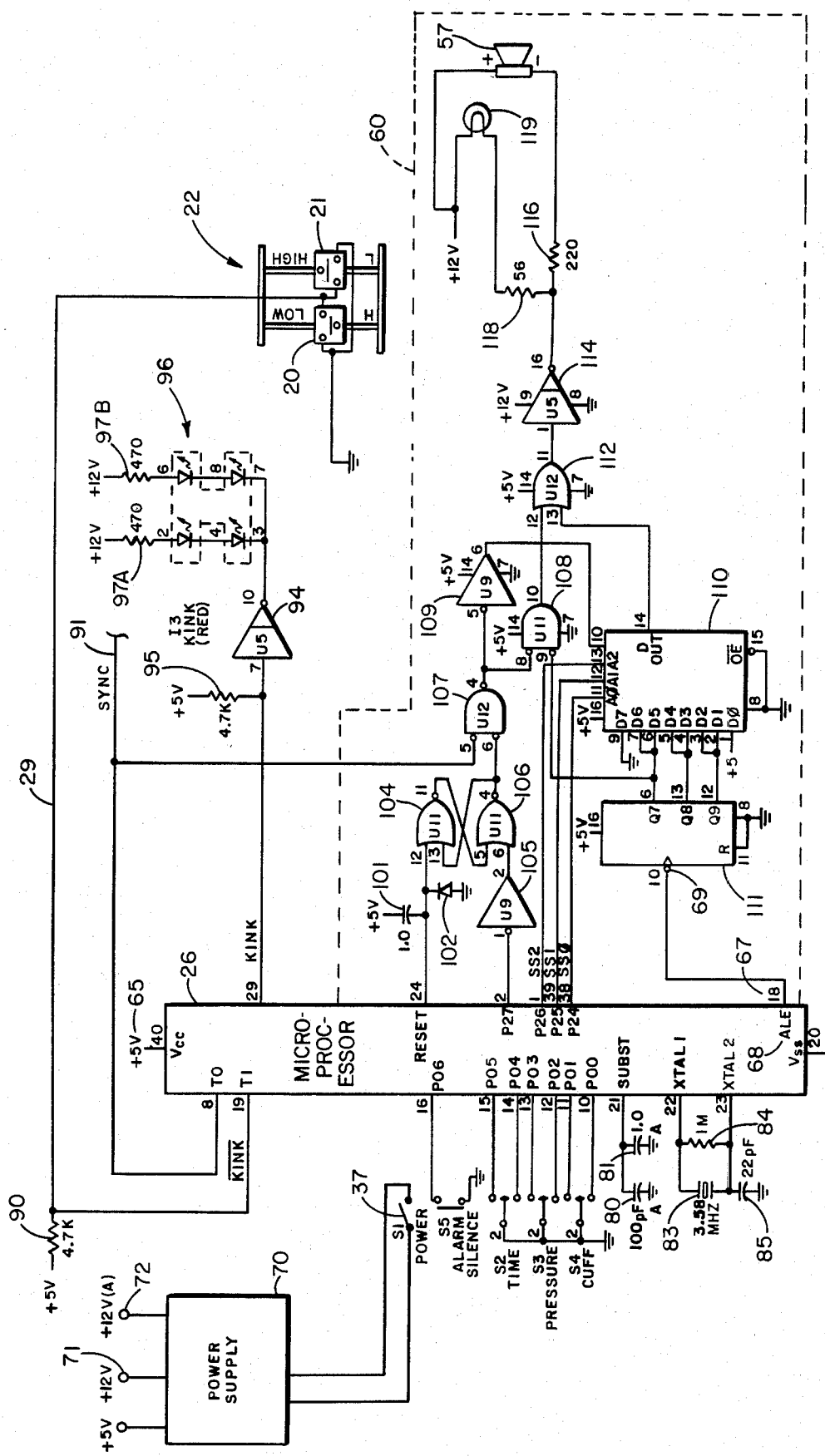
FIG. 2 shows the electronic circuitry of the preferred embodiment of the invention.

Turning now to FIG. 2, the detailed electrical circuitry of the invention is shown. The circuitry shown is that relating to the differential pressure means. Conventional circuitry may be used for the other portions of the tourniquet shown in FIG. 1, or circuitry as described in U.S. patent applications Ser. Nos. 485,546 and 485,548, companion applications to the present application, may be used.

The various electrical components in FIG. 2b are shown by their conventional draftsman symbols whenever these are available. For example, a voltage input is shown by the value of the voltage given at the end of a line such as at 65. A ground is shown at 66. The number, such as at 67, next to an input line to a component indicates the pin number of the component to which the line is attached. The notation, such as at 68, on the inside of an electrical component next to a connecting line, identifies the signal which is applied to the line by the internal circuitry of the electronic device, which identification shall be useful in discussion of the programming and other internal workings of these components below. An open circle, such as at 69, at an input or output indicates that the input or output is inverted.

Power supply 70, which includes AC line 32 (FIG. 2) and 12-volt battery 33, includes a 5-volt regulated output and two 12-volt outputs, one (71) of which is for the digital circuitry and the other (72) which is for the analog circuitry. Switch 37, located on the exterior panel of the tourniquet, applies power to the various components of the tourniquet through the power supply 70. Switches S2, S3, S4, and S5, also located on the front panel of the tourniquet, provide for manual input of commands to microprocessor 26. Closing switch S2 in the upwards direction puts a ground signal on pin 15 of microprocessor 26 which causes the microprocessor to increase the tourniquet time setting, while closing switch S2 in the downward position puts a ground on pin 14 of the microprocessor 26 which decreases the time setting. Likewise, switch S3 may be used to increase and decrease the pressure setting of the microprocessor via signals on pins 13 and 12, and switch S4 may be used to inflate and deflate the cuff via signals applied on pins 11 and 10 respectively of the microprocessor. Closing switch S5 pus a ground on pin 16 of the microprocessor which silences the alarm, which shall be discussed further below.

Quartz crystal circuit 63 includes piezoelectric crystal 83, resistor 84, and capacitor 85. Pin 21 of microprocessor 26 is connected to the analog ground through parallel capacitors 80 and 81. Resistor 84 and piezoelectric crystal 83 are connected in parallel across pins 22 and 23 of microprocessor 26. Pin 23 of microprocessor 26 is also connected to ground through capacitor 85.

One terminal of differential pressure switches 20 and 21 is connected to ground, while the other terminal is connected to line 29, which is connected to the +5 voltage source through resistor 90, and which is also applied to the number 19 input terminal of microprocessor 26. Line 91 connects to the watchdog timer 64 (FIG. 1) to provide an out-of-sync signal to pin 8 of microprocessor 26. The number 20 pin of microprocessor 26 is connected to ground while pin 40 is connected to the +5 voltage source.

Output pin 29 of microprocessor 26 is connected to the input terminal 7 of inverter 94. Input terminal 7 of inverter 94 is also connected to the +5 voltage source through resistor 95. The output of inverter 94 is connected through two pairs of light emitting diodes 96 through resistors 97a and 97b to the 12-volt voltage source. Each pair of the diodes 96 is connected in series, with the 12-volt voltage source connected to the anode of one diode and the cathode of the second diode being connected to the output of inverter 94.

The alarm circuitry 60 is shown within the dotted line in FIG. 2. Output pin 24 of microprocessor 26 is connected to the 5-volt voltage source through capacitor 101 and to the cathode of diode 102, which has its anode connected to the ground. Pin 24 is also connected to one input of NOR gate 104. The number 2 output of microprocessor 26 is connected to the input of inverter 105, the output of which is connected to one of the inputs of NOR gate 106. The output of NOR gate 104 is connected to one of the inputs of NOR gate 106 while the output of NOR gate 106 is connected to one of the inputs of NOR gate 104. The output of NOR gate 106 is connected to one of the inputs of negative input NAND gate 107. The other input of gate 107 is connected to the sync line 91. The output of negative input NAND gate 107 is applied to one of the inputs of negative input AND gate 108, and also to the input of inverter 109. The output of inverter 109 is applied to the number 10 input pin of 8-channel data selector 110. As will be discussed below, inverter 109 is part of a integrated circuit chip having six inverters on it; pin 14 of that chip is attached to the positive 5-volt voltage source and pin 7 of that chip is connected to ground. Likewise, negative input AND gate 108 is part of an integrated circuit chip having the 14 pin attached to the 5-volt voltage source and the 7 pin grounded. The output of negative input AND gate 108 is applied to one of the inputs of OR gate 112. OR gate 112 is also part of a larger integrated circuit chip having the 14 pin attached to the positive 5-volt voltage source and the 7 pin grounded. The output of OR gate 112 is applied to the input of open collector inverter 114, which also is part of a larger chip which has its 9 pin attached to the 12-volt voltage source and its 8 pin grounded. The output of inverter 114 is connected to the 12-volt positive power supply through a pair of parallel circuits, one of which includes resistor 116 connected in series with speaker 57 and the other of which includes resistor 118 in series with light bulb 119. The number 1, 39, and 38 output pins of microprocessor 26 are connected to the 13, 12, and 11 input pins respectively of 8-channel data selector 110. The number 18 pin of microprocessor 26 is connected to the inverted number 10 input of 14 stage divider 111. The number 8 and 11 pins of divider 111 are grounded while the number 16 pin is connected to the 5-volt voltage source. Output pin 6 of divider 111 is connected to the number 6 and 7 input pins of data selector 110 and also to one of the inputs to negative input AND gate 108. The number 13 output pin of divider 111 is connected to the number 4 and 5 input pins of data selector 110, and the number 12 output pin of divider 111 is connected to the number 2 and 3 input pins of data selector 110. The number 8, 9, and 15 pins of data selector 110 are grounded, while the number 1 and 16 pins are connected to the 5-volt voltage source. The number 14 output pin of data selector 110 is connected to one of the inputs of OR gate 112.

The components of the invention may be purchased from many sources. Kink switches 20 and 21 are preferably Fairchild PSF100A-20C differential pressure switches available from Fairchild/Schlumberger, 75 Mall Drive, Commack, N.Y. 11725. Valves 48 and 13 are preferably Clippard Model EVO-3-12 valves and may be obtained from Clippard Instrument laboratories, Inc., 7390 Colerain Road, Cincinnati, Ohio. The muffled vents 51 and 52 are preferably Clippard #1507 mufflers. Valve 54 is preferably a Clippard CS-30-393 light spring regulator. The motor is preferably a 12-volt DC motor, and the pump may be any one of a variety of fluid pumps and preferably the pump described in a companion application to the present application.

Transducer 18 is a Foxboro series 1800 transducer. Switch S5 is a single-pole, single-throw switch, while switches S2, S3, and S4 are single-pole, double-throw, center-off switches. Crystal 83 is preferably a 3.58 MHZ crystal. Microprocessor 26 is preferably an Intel 8022 single component 8-bit microcomputer with on-chip A/D converter, available from Intel Corporation, 3065 Bowers Avenue, Santa Clara, Calif. 95051. Inverter 94 is part of a Darlington transistor array with the identification ULN2003. The four LEDs may be bought in a package of four LEDs available from Hewlett Packard and called LED bar lights. Inverter 105 is part of a hex inverter chip type 4069. Gates 104, 106, and 108 are part of a quad NOR package type 4001. Inverter 109 is part of the same package as inverter 105. Gate 112 is actually purchased as a CMOS Quad OR gate package type 4071. Divider 111 is a 14-bit ripple counter type 4020. Data selector 110 is an 8-line to 1-line digital multiplexer type 4512. Speaker 57 is preferably a 2½ inch 100 ohm speaker, and bulb 119 may be any bulb capable of operating effectively at 12-volts. Although the above components are those used in the preferred embodiment, those skilled in the art will be aware of many equivalent components that may be substituted. Conventional components well known in the art may be used for all those parts of the invention that have not been expressly designated.

A specification and description is available with the Intel 8022 microprocessor, and any other microprocessor that can be substituted in the invention. Using this specification and description, and the knowledge generally available with respect to the programming of such microprocessors, suitable programs for carrying out the invention can be constructed following the above disclosure. Many such programs are possible. We shall discuss below the preferred embodiment of such a program that has been implemented to carry out the invention.

Figure 3A:
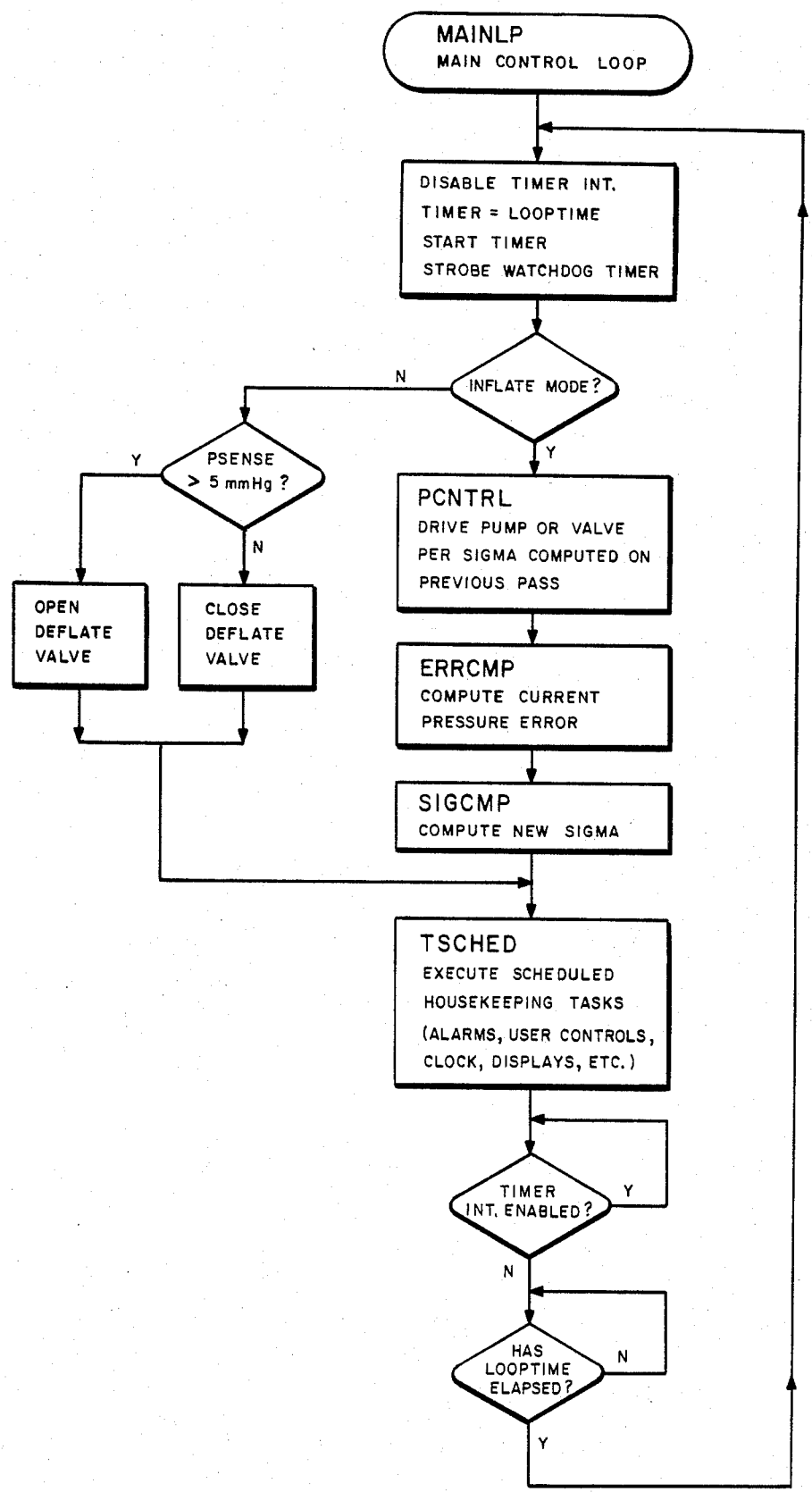
FIG. 3a through 3c are flow diagrams describing the preferred embodiment of the microprocessor programming according to the invention.

The main loop of the program is shown in FIG. 3a. This program controls the timing of the running of the motor 19 and the opening and closing of valve 20 to control the pressure in cuff 10. The timing of the main loop is controlled by an internal microprocessor timer which causes the loop to repeat with a period, $T_L$, of 34 milliseconds as shall be described below. Within the loop a time $T_{pw}$ is calculated, which is the pulse width time, i.e. the time over which the motor may be on or the valve 20 may be open. On the next loop after which the time $T_{pw}$ is calculated, the pump 12 or valve 13 may be energized from the time $T_o$ to $T_{pw}$. At the time $T_{pw}$ the internal microprocessor timer generates an interrupt to the microprocessor control, and the same timer is loaded to finish the loop, i.e. to continue for the time $(T_L - T_{pw})$.

Figure 3B:
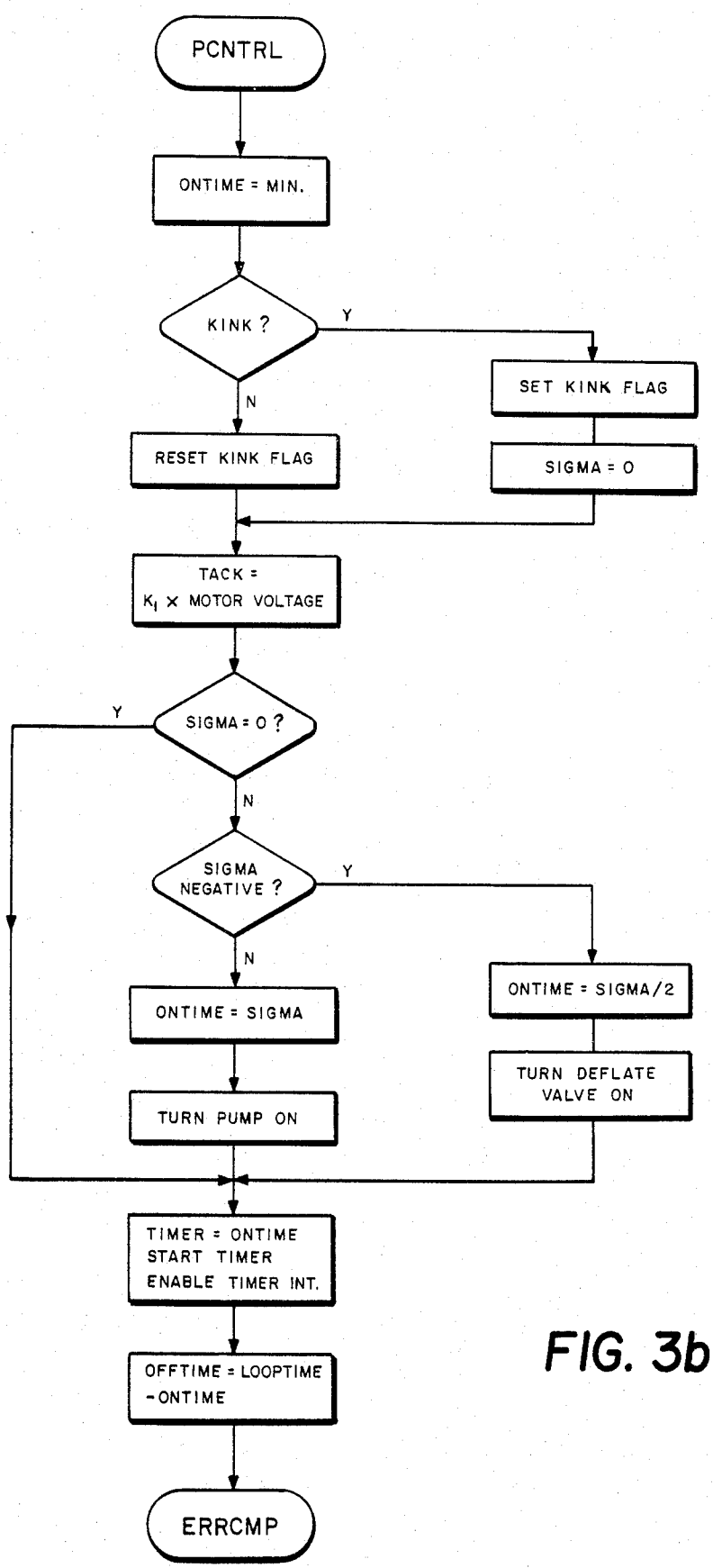

Turning now to a more detailed description of the program, in reference to FIGS. 1, 2a, 2b, and 3a, the program first resets both the internal microprocessor timer and the watchdog timer. The watchdog timer is set by a strobe signal from the microprocessor which is produced by a sub-program WDTSTB. If the operator has indicated that the cuff is to be deflated, the internal timer is set to $T_L$ and, if the sensed cuff pressure exceeds 5 mmHg, the deflate valve is opened. If the operator has indicated that the cuff should be inflated, the program control passes to the PCNTRL program (see FIG. 3b). The PCNTRL program first checks the T1 signal (microprocessor input line 19) to determine if there is a blockage in the tourniquet fluid system. If there is a blockage, the timer is loaded with the minimum time (MIN) necessary to complete housekeeping functions and the motor and valves are not activated. If there is no kink, the timer is loaded with the time $T_{pw}$ that was calculated on the previous loop and is stored in the microprocessor memory. The program then checks the pressure error, and if it is high, the valve 13 is turned on; if the pressure error is not high the pump 12 is turned on. After either the valve 13 is on or the pump 12 is on the program then starts the internal timer in the interrupt mode. The program control then passes to the ERRCMP program.

Figure 3C:
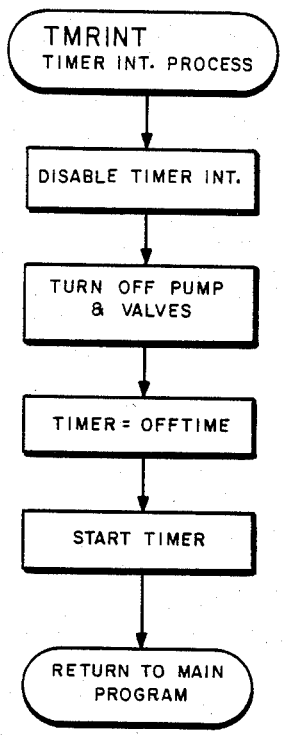

The timer will generate an interrupt when the programmed period has elapsed. This programmed period will be 265 microseconds times the number (ONTIME) the timer is loaded with, since the 8022 microprocessor increments its values every 265 microseconds. This time, $T_{pw}$, will be equal to MIN×265 microseconds=265 microseconds if a kink was detected (see above), SIGMA×265 microseconds if the motor 19 is to be turned on, or -(SIGMA/2)×265 microseconds if the valve 20 is to be turned on. The interrupt causes normal program execution to cease temporarily and the timer interrupt routine (FIG. 3c) to be executed. This routine will turn off both the motor/pump 11/12 and deflate valve 13, disable the timer interrupt and restart the timer with a value OFFTIME=$T_L - T_{pw}$. Control then returns to the point in the main program at which the interrupt occurred.

Program control passes from the PCNTRL program to the ERRCMP sub-program which calculates the pressure error, and then to the SIGCMP sub-program which computes the pressure adjustment factor SIGMA for the next loop. Control then passes to the housekeeping sub-program TSCHED. As mentioned above, in the PCNTRL program, a flag is set if the T1 (pin 19) signal is low. As long as this flag is low the housekeeping program will cause the output pin 29 of the microprocessor to go high once each cycle of the main loop which will cause the LEDs 96 to flash about three times a second. The housekeeping functions also cause an appropriate one of pins P24 through P26 to go low which causes a sound alarm as shall be described further below. When the housekeeping functions are finished, the main program continues to loop until the interrupt time, whereupon the pump or valve is turned off (FIG. 3c), and the timer is loaded with the remaining time Thd L−$T_{pw}$=OFFTIME. The timer is started again in the no interrupt mode, and when the timer times out control returns to the beginning of the main loop (FIG. 3a).

The circuitry 60 enclosed in the dotted line to the right of the microprocessor in FIG. 2 includes the sound generator 58 and the alarm silence indicator 61. The circuitry 60 is used to produce audible tones in conjunction with the various alarm conditions that the tourniquet is capable of detecting and announcing, and to produce a visual indication that the sound has been suppressed when the alarm silence switch S5 is pressed. The frequencies of the available tones are 233 Hz, 466 Hz and 932 Hz, the highest of which is the "kink" alarm. The frequencies are generated by a 14-bit ripple counter 111, which divides the 119.32 KHz ALE signal from the microprocessor 26 (pin 18). The divided ALE signals are applied to the data inputs of 8-to-1 multiplexer data selector 110. The tone frequency to be produced at pin 14 of data selector 110 is determined by the states of the sound select signals (SS0, SS1 and SS2) that are applied to the address inputs (A0, A1, A2) of selector 110. The sound select signals are developed by the microprocessor on pins 38, 39, and 1 respectively.

When no tone is desired, and the watchdog timer is satisfied (line 91 is high), data input 7 to selector 110 is selected by setting all three sound select lines high. That results in a low level output from pin 14 which when fed to the input of gate 112 (pin 13) along with a zero input on pin 12 results in a high level output from the inverter 114 (pin 16), hence no sound or alarm silence light.

When the kink line 29 is low the p24, p25, p26 signal in microprocessor 26 becomes a binary 5. That is, pin 38 and pin 1 go high and pin 39 goes low. This binary 5 signal is passed to the selector 110 which selects the D5 input (pin 6) for application as its D out signal (pin 14). Thus the 932 Hz signal from pin 6 of counter 111 is passed through gate 112 to driver inverter 114 to produce the 932 Hz alarm signal.

When an alarm condition exists and the Alarm Silence switch has been pressed, all sound select lines are made low. This causes selector 110 to select the +5 V level on its D0 input to appear at its output on pin 14. This causes the output of inverter 114 to be held low. In this state the Alarm Silence light will remain lit, however, there will be no sound since DC is being supplied to the speaker. Power dissipation in the speaker is limited by resistor 116.

The differential pressure switches 20 and 21 cooperate by completing the circuit between their input and output when the pressure becomes higher at the side of the switch indicated by the term "high" (FIG. 1) as compared to the side of the switch indicated by the term "low". Since the input terminal is grounded, the closing of the switch will produce the low signal on the microprocessor pin 19 as discussed above. As is clear from FIG. 1, switch 20 will close when the pressure transducer side of the tourniquet is a higher pressure than the inflate/deflate side, and switch 21 will close when the inflate/deflate side of the tourniquet is at a higher pressure than the pressure sensing side. The fact that witch 21 indicates a pressure differential in the opposite direction to kink switch 21 is referred to as an anti-parallel connection of the switches between the ports 14 and 19. It is a feature of the invention that this anti-parallel connection ensures recognition of an obstruction in either side of the tubing.

Preferably the pressure difference at which the differential pressure switches 20 and 21 are activated is preferably about 37 mmHg+/−20%. This enables any kink that would have an effect on the tourniquet to be detected, yet is high enough so that fast inflation rates will not create pressure differences that might activate the detector.

A novel pneumatic tourniquet that provides for improved detection of obstructions in the tourniquet tubing system, and has numerous other features and advantages has been described. While the above has been referenced to a particular embodiment, it is evident that, now that the advantages of using anit-parallel pressure differential switches between the ports of the tourniquet have been disclosed, those skilled in the art can now make numerous uses of, modifications of, and departures from these specific embodiments described herein without departing from the inventive concepts. For example, many other features may be added to the tourniquet, or some of the features that have been described may be eliminated. Likewise, substitutions may be made for most of the parts. Consequently the invention is to be construed as embracing each and every novel feature and novel combination of features within the appended claims.

What we claim is:

1. A pneumatic tourniquet comprising:
a first means for inflating and deflating a tourniquet cuff, said means having a first port for connection to said cuff;
a second means for sensing the pressure in said cuff, said means having a second port for connection to said cuff;
a pair of pressure differential switches connected anti-parallelly between said first and second means for producing a signal indicative of a pressure differential between said first and second means; and
means responsive to said signal for producing an alarm.

2. A pneumatic tourniquet as in claim 1 wherein said pressure differential switches produce a signal when the magnitude of said pressure difference between said first and second means exceeds a predetermined amount.

3. A pneumatic tourniquet as in claim 2 wherein said predetermined about is between 20 mmHg and 40 mmHg.

4. A pneumatic tourniquet as in claim 1 and further comprising means responsive to said signal for deactivating said means for inflating and deflating said cuff.

* * * * *